United States Patent
Ajani et al.

(10) Patent No.: US 6,770,653 B2
(45) Date of Patent: Aug. 3, 2004

(54) METHOD AND DOSAGE FORM FOR TREATING TUMORS BY THE ADMINISTRATION OF TEGAFUR, URACIL, FOLINIC ACID, PACLITAXEL AND CARBOPLATIN

(75) Inventors: Jafferhusen Abdulhusen Ajani, Houston, TX (US); Steven E. Benner, Titusville, NJ (US); Terry S. Dugan, Plainsboro, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/090,354

(22) Filed: Mar. 4, 2002

(65) Prior Publication Data

US 2002/0173482 A1 Nov. 21, 2002

(Under 37 CFR 1.47)

Related U.S. Application Data

(60) Provisional application No. 60/273,577, filed on Mar. 6, 2001.

(51) Int. Cl.$^7$ .............................................. A61K 31/505
(52) U.S. Cl. ........................ 514/274; 514/249; 514/449; 514/492; 514/836; 514/922
(58) Field of Search ................................ 514/274, 249, 514/449, 492, 836, 922

(56) References Cited

U.S. PATENT DOCUMENTS

| 4,328,229 A | | 5/1982 | Fujii et al. |
| 5,534,513 A | | 7/1996 | Junji et al. |
| 5,919,816 A | * | 7/1999 | Hausheer et al. ............ 514/449 |
| 6,239,167 B1 | * | 5/2001 | Bissery ....................... 514/449 |

OTHER PUBLICATIONS

Database HCAPLUS on ACS, Accession No. 2000:103596, Langer, The role of tegafur/uracil in pulmonary maligancy, Abstract, 1999, 58 (3), pp. 71–75.
Database HCAPLUS on ACS, Accession No. 2000:131659, Hoff et al., Tegafur/uracil +calcium folinate in colorectal cancer: Double modulation of fluorouracil. Abstract, 1999, 58 (3), pp. 77–83.
Database HCAPLUS on ACS, Accession No. 2000:103599, Brockstein et al., Oral chemotherapy in head and neck cancer, Abstract, 1999, 58 (3) pp. 91–97.
Database MEDLINE on ACS, Accession No. 94189518, Grau et al., Carboplatin plus ftorafur as a palliative treatment in locally advanced cancer on the oral cavity and lip., Apr. 1994, 17(2) pp. 134–136.

* cited by examiner

*Primary Examiner*—Frederick F. Krass
(74) *Attorney, Agent, or Firm*—Maureen S. Gibbons

(57) ABSTRACT

This invention provides a method of treating a tumor in a warm-blooded animal by administering an anti-tumor effective amount of tegafur, uracil, folinic acid, paclitaxel and carboplatin.

12 Claims, No Drawings

METHOD AND DOSAGE FORM FOR TREATING TUMORS BY THE ADMINISTRATION OF TEGAFUR, URACIL, FOLINIC ACID, PACLITAXEL AND CARBOPLATIN

RELATED APPLICATIONS

This application claims the benefit of U.S. Provisional Patent Application No. 60/273,577, filed Mar. 6, 2001.

FIELD OF THE INVENTION

The present invention is directed to the administration to a warm blooded animal of the combination of tegafur, uracil, folinic acid, paclitaxel and carboplatin for the treatment of tumors.

BACKGROUND OF THE INVENTION

5-Fluorouracil (5-FU) is a known anti-tumor agent. The combination of 5-fluorouracil and folinic acid is a known treatment for colorectal cancer. Tegafur (1-(2-tertrahydrofuryl)-5-fluorouracil) is a prodrug of 5-fluorouracil. In vivo, 5-fluorouracil is rapidly inactivated by the enzyme dihydropyridine dehydrogenase (DPD). Uracil competitively inhibits DPD metabolism of 5-FU generated from tegafur. Thus, coadministration of uracil with tegafur results in higher exposures of active 5-FU as compared to tegafur alone. It is known that 5-fluorouracil cannot be administered orally.

U.S. Pat. No. 4,328,229 discloses an anti-cancer composition containing 1-(2-tetrahydrofuryl)-5-fluorouracil ("tegafur") and uracil. The composition is used for delivery of 5-fluorouracil to a tumor sensitive to 5-fluorouracil in a warm-blooded animal. It is disclosed that the composition can be administered in a variety of dosage forms including an oral dosage form.

U.S. Pat. No. 5,534,513 discloses an anti-tumor composition containing tegafur and uracil in a molar ratio of 1:4. This anti-tumor composition is stated to be further potentiated by the administration of folinic acid or a pharmaceutically acceptable salt thereof. It is disclosed in the '513 patent that the combination can be administered in a variety of dosage forms including an oral dosage form.

Paclitaxel (TAXOL®), a diterpene taxane compound, is a natural substance extracted from the bark of the Pacific yew tree, *Taxus brevifolia*. In studies, it has been shown to possess excellent antitumor activity against a range of tumors in in vivo animal models including ovarian and breast, for example. Paclitaxel is an antimitotic agent which preferentially binds to microtubules. The stabilization of microtubules by paclitaxel inhibits reorganization of the microtubule network. Paclitaxel is typically administered by intravenous injection or infusion.

Carboplatin (PARAPLATIN®) is a known anti-tumor agent which induces both protein and non-protein associated DNA cross-links. This effect is observed to be cell-cycle nonspecific. Carboplatin is typically administered by intravenous infusion or injection.

It has been observed by Applicants that 5-fluorouracil can enhance the activity of paclitaxel and carboplatin. However, because 5-fluorouracil cannot be administered orally, the mode of administration for this combination therapy requires a more invasive form of administration such as through intravenous injection, and therefore typically requires administration by trained medical personnel.

It would be an advance in the art of treating tumors, especially tumors of the esophagus, gastroesophageal junction, and stomach, if a therapy could be developed employing the intravenous administration of paclitaxel and carboplatin, and oral administration of 5-fluorouracil to a warm-blooded animal for the effective treatment of such tumors.

SUMMARY OF THE INVENTION

The present invention is generally directed to the administration of tegafur, uracil, folinic acid or a pharmaceutically acceptable salt thereof, paclitaxel and carboplatin in suitable dosage forms to warm-blooded animals for the treatment of tumors, especially tumors of the esophagus, gastroesophageal junction, and stomach. In a particular aspect of the present invention, tegafur, uracil and folinic acid or a pharmaceutically acceptable salt thereof are administered in oral dosage form(s) to a warm-blooded animal having a tumor, and paclitaxel and carboplatin are intravenously administered to the warm-blooded animal. In a preferred embodiment of the invention, tegafur and uracil are present in respective amounts sufficient for tegafur to effectively and efficiently convert to 5-fluorouracil. In a particularly preferred embodiment of the invention tegafur and uracil are present in a molar ratio of about 1:4 (hereinafter referred to as "UFT").

There is also disclosed a method of treating cancer by orally administering an anti-tumor effective amount of the combination of tegafur and uracil, preferably as UFT, and folinic acid or a pharmaceutically acceptable salt thereof to a warm-blooded animal having a tumor who is undergoing paclitaxel and carboplatin combination therapy.

DETAILED DESCRIPTION OF THE INVENTION

The combination of tegafur and uracil in amounts sufficient to convert tegafur to 5-fluorouracil (preferably a molar ratio of about 1:4) can be administered orally. It was discovered that oral administration of this combination produced sufficient 5-fluorouracil and along with paclitaxel and carboplatin would provide a potent and effective treatment of tumors especially those associated with tumors of the esophagus, gastroesophageal junction, and stomach.

In one oral dosage form of the present invention, tegafur, uracil, and folinic acid, preferably provided as the calcium salt "calcium folinate," are present in a single oral dosage form. Alternatively, and preferably, tegafur and uracil are provided in a first oral dosage form, and folinic acid, preferably provided as calcium folinate, is provided in a second oral dosage form. The dosage of each active ingredient for administration on a daily basis is from about 0.1 to 100 mg/kg/day, preferably about 1 to 30 mg/kg/day for tegafur. The preferred dosage for uracil is from about 1 to 50 mg/kg/day. For UFT, i.e. the 1:4 combination of tegafur and uracil, the dosage is from about 100 to 500 $mg/m^2$/day based on tegafur, preferably from about 200 to 300 $mg/m^2$/day based on tegafur. Folinic acid or a pharmaceutically acceptable salt thereof may be administered in an amount from about 0.1 to 500 mg/kg/day, but preferably is administered as calcium folinate in a fixed dose of about 90 mg/day. The oral dosage form(s) may be administered in a single dose or in divided doses typically up to 3 times a day.

Paclitaxel and carboplatin are each preferably administered non-orally, more preferably by intravenous infusion. Based on body surface area, the infusion dosage of paclitaxel may range from about 10 to 300 $mg/m^2$, preferably from about 30 to 200 $mg/m^2$ and more preferably about 100, 135 or 175 $mg/m^2$. Paclitaxel infusions should be preceded with appropriate premedications known to those skilled in the art. The paclitaxel dosage is preferably administered intravenously by infusion over a period of at least about 3 hours, preferably over a period of about 3 or 24 hours. The carboplatin dosage is preferably administered intravenously by infusion, preferably over a period of at least about 15 minutes. The infusion dosage of carboplatin may range from about 100 to 500 mg/m², preferably about 300 or 360 mg/m². Alternatively, the infusion dosage of carboplatin is calculated by the Calvert formula to provide a target AUC of about 4 to 6 mg/mL·min.

Those of ordinary skill in the art would have the knowledge to adjust the above stated dosage ranges for UFT, folinic acid or a pharmaceutically acceptable salt thereof, paclitaxel as needed based, for example, on body surface and/or in the event of toxicity and for carboplatin based on the Calvert formula as described below. In accordance with the present invention, the combination of tegafur and uracil (e.g. UFT) results in a sufficient amount of 5-fluorouracil available in combination with paclitaxel and carboplatin to provide an effective treatment of tumors, especially tumors of the esophagus, gastroesophageal junction, and stomach in a minimally invasive manner.

In a preferred embodiment, the present invention provides a method of treating cancer, particularly cancerous tumors, in a warm-blooded animal which method comprises administering the active agents in a regimen typically based on a twenty-eight day cycle. By way of example, paclitaxel at a dose of about 100, 135, or 175 mg/m², preferably about 175 mg/m², and carboplatin at a dose of about 300 or 360 mg/m², or at a dose corresponding to a target area under the concentration-curve (AUC) of about 4 to 6 mg/mL·min, preferably about 6 mg/mL·min, as determined by the Calvert formula, may each be intravenously administered on day 1 of the twenty-eight day cycle, and UFT at a dose of about 200, 250, or 300 mg/m²/day based on tegafur and calcium folinate at a dose of about 90 mg/day may be administered on days 2 through 22, followed by no administration of the active agents on days 23 through 28. The twenty-eight day cycle may be repeated as necessary. The carboplatin dosage is calculated prior to each course of therapy through the use of the Calvert formula as represented below:

Carboplatin in mg (total dose)=(target $AUC$)×($GFR$+25)

The target AUC is about 4 to 6 mg/mL·min. The glomerular filtration rate (GFR in mL/min) is approximated by measuring the creatinine clearance (Cr. Cl.) of the patient which is calculated from the patient's age (years), weight (kilograms), and serum creatinine level (mg/dL) through use of the Crockroft-Gault formula as represented below:

$$\text{Cr. Cl. (males)} = \frac{(140 - \text{age}) \times \text{weight}}{\text{Serum Creatinine}} \times 72$$

Cr. Cl. (females)=0.85×[Cr. Cl. (males)].

The dosage forms may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Dosage forms for oral administration include tablets, powders, granules, and the like. Excipients and additives which may be used include, but are not limited to, lactose, sucrose, sodium chloride, glucose, urea, starch, calcium, kaolin, crystalline cellulose, salicylic acid, methylcellulose, glycerol, sodium alginate, arabic gum and the like. Conventional binders may be used such as glucose solutions, starch solutions, gelatine solutions, and the like. Disintegrators may be used including, but not limited to, dry starch, sodium alginate, agar powder, calcium carbonate, and the like. Absorbents which may be used include, but are not limited to, starch, lactose, kaolin, bentonite, and the like. Lubricants which may be used include, but are not limited to, purified talc, stearic acid salts, boric acid powder, polyethylene glycol and the like.

Dosage forms for parenteral administration such as by subcutaneous, intravenous, intramuscular, or intrasternal injection or infusion techniques, include injectable solutions or suspensions which may contain, for example, pharmaceutically acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

The following examples are exemplary of the claimed invention, but are not intended to limit the invention as encompassed by the full disclosure of the invention set forth herein.

EXAMPLE 1

This study assessed the in vivo dose-limiting toxicity of UFT (tegafur and uracil in a molar ratio of 1:4) plus calcium folinate when given 3 times per day for 21 days, in combination with TAXOL® (single dose, infused over 3-hours, on Day 1 of cycle) and PARAPLATIN® (single dose, infused over 1 hour on Day 1 of cycle) in patients with cancer of the esophagus, stomach or gastroesophageal junction, and defined the recommended dose to be used in the Phase II portion of the study.

A standard phase I trial was assessed with escalating doses of UFT with a fixed dose of calcium folinate (leucovorin) at 90 mg/day, TAXOL® at a fixed dose of 175 mg/m², given as a 3 hour infusion on Day 1, and PARAPLATIN® at a dose corresponding to a target area under the curve (AUC) value of about 6 mg/mL·min calculated by the Calvert formula infused over 1 hour. The initial dose of UFT was 200 mg/m²/day based on tegafur, given with leucovorin 90 mg/day, both divided into 3 daily doses for 21 days, beginning on Day 2, followed by a 6-day period of rest.

UFT doses were escalated in cohorts of 3 to 6 patients. The dose and schedule of leucovorin was kept constant. Dose escalation of UFT was performed until the first dose level in which ≧2 of the first 3 patients or ≧2 of 6 patients at that dose level experience dose limiting toxicities (the highest administered dose limited by toxicity). The next immediately lower dose level, the maximum tolerated dose (MTD), would be recommended for Phase II testing. Cohorts of at least 3 evaluable patients comprised the test patient study, were enrolled at UFT dose levels of: 200 (DL200), 250 (DL250), or 300 (DL300) mg/m²/day based on tegafur.

Entry criteria for the study included, but was not limited to, a histological or cytological confirmed metastatic or unresectable local-regional squamous cell carcinoma or adenocarcinoma of the esophagus or gastroesophageal junction, or adenocarcinoma of the stomach, no concurrent radiotherapy treatment, no prior chemotherapy treatment for metastatic disease, ECOG performance status of 0–2, no brain metastatic disease, and adequate hematological, renal and hepatic function.

The treatments were administered on a four-week cycle until progressive disease or unacceptable toxicity occurred. TAXOL® was infused at a dose amount of 175 mg/m² over a 3 hour period, followed by PARAPLATIN® administered intravenously at a target area under the concentration curve (AUC) of about 6 mg/mL·min as determined by the Calvert formula described below, on Day 1 of each cycle. Then, UFT and leucovorin were given orally on days 2–22 of each cycle, followed by 6 days of rest. The initial dose of UFT was 200 mg/m²/day based on tegafur, divided into three daily doses. The leucovorin dose was fixed at 90 mg/day, divided into 3 doses taken concurrently with UFT at 8 hour intervals. Treatment cycles were repeated every 28 days.

The PARAPLATIN® dosage was calculated prior to each course of therapy for each patient using the following procedure. The PARAPLATIN® dosage calculation was determined using the Calvert formula:

PARAPLATIN® in mg=(target $AUC$)×($GFR$+25)

The value of the target AUC is about 6 mg/mL·min. The value of the glomerular filtration rate (GFR in mL/min) was approximated by measuring the creatinine clearance (Cr. Cl.) of the patient which was calculated from the age in years, weight in kilograms, and serum creatinine in mg/dL of the patient with the Crockroft-Gault formula:

$$Cr.\ Cl.\ (males) = \frac{(140 - age) \times weight}{Serum\ Creatinine} \times 72$$

$Cr.\ Cl.\ (females) = 0.85 \times [Cr.\ Cl.\ (males)]$.

After all patients had safely completed one cycle of treatment, the dose of UFT was escalated. The study continued to each progressive level until the maximum tolerated dose (MTD) was experienced. The MTD was defined as the dose level at which greater than 1/3 or 2/6 of the patients experienced a dose limiting toxicity (DLT) during the first cycle of treatment.

The DLT was defined as follows:

Hematologic Toxicity
  a. Grade 3/4 neutropenia complicated by accompanying fever, or
  b. Grade 3/4 thrombocytopenia prolonged or complicated by bleeding or requiring platelet transfusion, or
  c. Grade 4 thrombocytopenia.

Non-Hematologic Toxicity
  a. Greater than grade 3 nausea, vomiting or diarrhea despite medical intervention, or
  b. Greater than grade 3 other non-hematologic toxicity, or
  c. inability to take ≧75% of the planned UFT/leucovorin dose, or
  d. delay in start of the next cycle of therapy by more than 2 weeks.

Patients qualified for the test protocol if they met the following criteria:

Histological or cytological confirmed metastatic or unresectable local-regional squamous cell carcinoma or adenocarcinoma of the esophagus or gastroesophageal junction, or adenocarcinoma of the stomach Measurable (>1.5 cm. in both dimensions) or evaluable disease (≧1.5 cm in at least one dimension)

Have adequate hematologic, hepatic, and renal function

Age >18 years

Either no prior chemotherapy or immunotherapy treatments, including adjuvant or neoadjuvant regimens ECOG performance status 0–2 (Zubrod scale), life expectancy >3 month Written informed consent Patients were disqualified from the test protocol if they had bowel obstruction, any condition which would affect UFT and/or leucovorin absorption, or prior radiotherapy sessions unless associated with palliative or adjuvant therapy treatments of metastatic or locally advanced malignancies adenocarcinoma or squamous cell carcinoma of the esophagus, gastoesophageal junction and/or stomach.

Sixteen patients were enrolled in the phase I study. Dose limiting toxicities were observed at cycle 1 in two patients. At DL200, one patient experienced Grade 3 nausea and vomiting leading to 32% missed UFT doses. At DL300, one patient experienced grade 3 myalgia. DL300 was considered tolerable and was expanded to 9 patients. In cycle 2, adverse events consistent with DLT included one patient with neutropenic fever corresponding with a greater than 14 day delay for platelet recovery, one patient with grade 3 fatigue, and one patient with grade 3 vomiting. In all cycles, other grade ≧3 adverse events observed included neutropenic fever, neuropathy, deep vein thrombosis, chills, vomiting, constipation, and fatigue. Clinical responses included: partial responses observed in 6 patients in which there is generally a decrease of at least 50% in the size of tumor lesions; and stable disease was observed in 4 patients where there was no change in the disease (i.e. a decrease in tumor size of less than 50% or an increase in tumor size of less than 25%). A progressive disease situation was observed in 5 patients. This category includes the appearance of any new, previously unidentified lesions or occurrence of malignant pleural effusion or ascites and/or an increase by at least 25% in the size of one or more measurable lesions. The treatment regimen described above was generally well tolerated and demonstrated anti-tumor activity at all dose levels. There was one patient where the response was not known.

What is claimed is:

1. A method of treating a tumor of the esophagus, gastroesophageal junction, or the stomach in a warm-blooded animal comprising administering to said warm-blooded animal in need thereof an anti-tumor effective amount of tegafur, uracil, folinic acid or pharmaceutically acceptable salt thereof, paclitaxel and carboplatin.

2. The method of claim 1 comprising orally administering each of tegafur, uracil, and folinic acid or a pharmaceutically acceptable salt thereof.

3. The method of claim 1 wherein the amount of tegafur and uracil is sufficient to produce an effective amount of 5-fluorouracil.

4. The method of claim 1 wherein tegafur and uracil are present in a molar ratio of about 1:4, respectively.

5. The method of claim 1 wherein paclitaxel and carboplatin are administered prior to tegafur, uracil, and folinic acid or a pharmaceutically acceptable salt thereof.

6. The method of claim 5 comprising a treatment schedule of about 28 days wherein paclitaxel and carboplatin are intravenously administered on day 1 and tegafur, uracil and folinic acid or a phannaceutically acceptable salt thereof, are orally administered on days 2 to 22, and days 23 to 28 are rest days.

7. The method of claim 6 wherein the treatment schedule is repeated at least once.

8. The method of claim 5 wherein tegafur and uracil are present in a molar ratio of about 1:4, respectively.

9. The method of claim 8 wherein the combination of tegafur and uracil is orally administered at a dosage of about 200 to 300 mg/m$^2$/day based on tegafur, calcium folinate is orally administered at a fixed dosage of about 90 mg/day, paclitaxel is intravenously administered at a dosage of about 30 to 200 mg/m$^2$, and carboplatin is intravenously administered at a dosage of about 100 to 500 mg/m$^2$ or at a dosage calculated by the Calvert formula to provide an AUC of about 4 to 6 mg/mL·min.

10. The method of claim 6 wherein tegafur and uracil are present in a molar ratio of 1:4, respectively.

11. The method of claim 10 wherein the combination of tegafur and uracil is orally administered at a dosage of about 200 to 300 mg/m$^2$/day based on tegafur, calcium folinate is orally administered at a fixed dosage of about 90 mg/day, paclitaxel is intravenously administered at a dosage of about 30 to 200 mg/m$^2$, and carboplatin is intravenously administered at a dosage of about 100 to 500 mg/m$^2$ or at a dosage calculated by the Calvert formula to provide an AUC of about 4 to 6 mg/mL·min.

12. The method of claim 1 wherein the warm-blooded animal is a human.

* * * * *